United States Patent [19]

Carstens

[11] 4,113,090
[45] Sep. 12, 1978

[54] MEDICAL INSTRUMENT PACKAGE

[75] Inventor: Dennis L. Carstens, Columbus, Nebr.

[73] Assignee: Becton, Dickinson and Company, East Rutherford, N.J.

[21] Appl. No.: 824,412

[22] Filed: Aug. 15, 1977

[51] Int. Cl.² .......................................... B65D 85/24
[52] U.S. Cl. .............................. 206/365; 206/210; 206/306; 206/571
[58] Field of Search ............... 220/8; 206/207, 210, 206/212, 339, 363, 365, 380, 382, 574, 306, 571

[56] References Cited

U.S. PATENT DOCUMENTS

| | | | |
|---|---|---|---|
| 3,021,942 | 2/1962 | Hamilton | 206/365 |
| 3,070,093 | 12/1962 | Sarnoff et al. | 206/222 |
| 3,101,841 | 8/1963 | Baldwin | 206/365 |
| 3,149,717 | 9/1964 | Castelli | 206/365 |
| 3,294,231 | 12/1966 | Vanderbeck | 206/365 |
| 3,329,146 | 7/1967 | Waldman, Jr. | 206/365 |
| 3,333,682 | 8/1967 | Burke | 206/210 |
| 3,342,319 | 9/1967 | Faulseit | 206/365 |
| 3,514,008 | 5/1970 | Dorn | 220/8 |

FOREIGN PATENT DOCUMENTS 717,777  9/1965  Canada .................................. 206/365

*Primary Examiner*—William Price
*Assistant Examiner*—Bruce H. Bernstein
*Attorney, Agent, or Firm*—Kane, Dalsimer, Kane, Sullivan & Kurucz

[57] ABSTRACT

A package for medical needle assemblies and the like including a shield, a cap, and a closure. The shield encloses the needle and a portion of the hub. The cap is mounted on the shield so that it is shiftable between two positions. In the first position it protects the exposed portion of the hub extending from the shield and in the second position it is slidable along the shield to expose the portion of the hub projecting from the shield to facilitate grasping and removal of the needle assembly from the package. The closure covers the opening in the cap and is removable when the package is opened. The closure in working cooperation with a sealing engagement between the cap and the shield seals the needle assembly in the package.

6 Claims, 6 Drawing Figures

U.S. Patent  Sept. 12, 1978  4,113,090
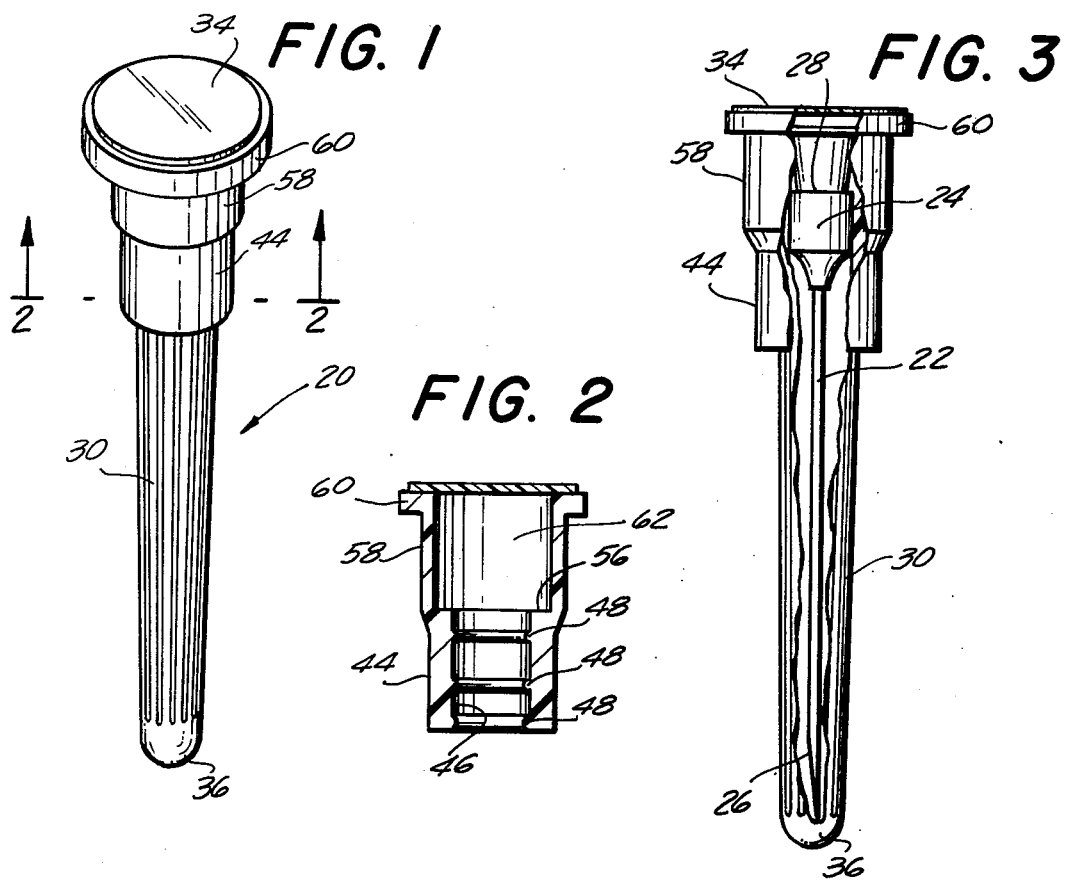
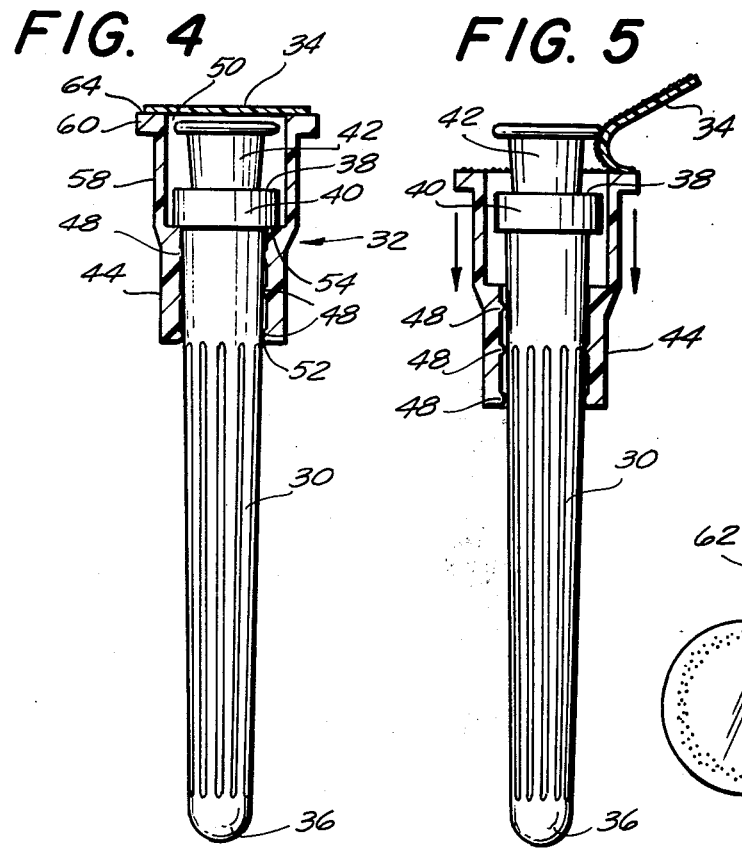

MEDICAL INSTRUMENT PACKAGE

BACKGROUND OF THE INVENTION

With medical instrument, for example disposable needles, it is often necessary to store the needles in a sterile condition for an extended period of time prior to use. The difficulty with many types of packages is that they are easily destructable particularly when containing a sharp pointed instrument. A "soft" package is easily pierceable by a needle thus destroying the integrity of the package and the sterility of the needle. On the other hand, the "soft" package is easy to open to gain access to the needle. This is of advantage in the medical field where time is often of the essence and also where sharp pointed items like needles are contained in the package. A needle which is difficult to grasp and remove from the package can produce accidental injury to the operator.

Accordingly, it has been found useful to employ a "hard" package for protecting instruments such as disposable needles. The "hard" package is a rigid support structure which protects the needle and avoids the danger of the needle puncturing the walls of the package and destroying the integrity and sterility of the interior. The difficulty with the "hard" package is access to the instrument when the package is open. It can be readily perceived how difficult it is to remove an item from a rigid container. This is particularly true when the item has a sharp point. Accidents can occur if the sharp object is not carefully handled. Therefore, it is advantageous to provide a "hard" package to protect a device such as a needle and also permit easy access to the needle when the package is to be opened and the needle removed and used. An example of one type of structure aimed at attaining the advantages of both the "hard" and the "soft" pack is disclosed in U.S. Pat. No. 3,342,319.

SUMMARY OF THE INVENTION

With the above background in mind, it is among the primary objectives of the present invention to provide a "hard" package for a medical device such as a needle which protects and supports the needle in packaged form and yet is easily shiftable to a position which permits easy access to the protected instrument at the time of use.

It is an objective to provide a "hard" package for a disposable medical instrument such as a needle assembly which is formed of low cost material for disposability purposes and which can be easily opened in a condition which presents the protected item in readily acceptable position for removal and use.

Furthermore, the package is designed for ease of sterilization in the packaged form and to retain sterility over a period of extensive handling and storage prior to use.

It is also contemplated that the package be designed with only three components, a shield, a cap, and a closure. The structure is designed so that interchangeability of caps is obtainable with the same shield in order to accommodate various size devices within the package. The package can only be opened through the closure or tab with the remaining components being rigid thereby providing positive tamper evidence. The package is designed so that the cap is shiftable with respect to the shield to expose a portion of the protected item when the package is opened to facilitate access and removal of the contained device. An appropriate seal is provided between the sliding surfaces on the cap and shield to maintain the integrity and sterility of the interior of the package prior to opening for use.

It is contemplated that the inexpensive disposable materials for the package structure can be of a common type used in the medical field such as polypropylene plastic for the shield, polyethylene plastic for the cap and a surgical grade paper for the tab or closure. Naturally a conventional substitute for these materials can be employed.

An ultimate objective is to provide a rigid package for facilitating the sterilization of a medical instrument contained therein, protecting the medical instrument in a rigid protective package during shipping, handling and storage, and permitting easy opening and access to the contained structure when use is desired. The package is easy to open and the user requires few hand motions in the opening process. With the materials used an attractive package can be provided. The package can be designed with a fiber-free peel action due to the ability to employ a paper tab for the closure. Furthermore, the parts of the package can easily be assembled during the packaging procedure. The package is designed for conventional sterilization procedure such as E.T.O. sterilization through the paper closure. The paper closure can be attached to the rigid portion of the package by conventional means such as use of an appropriate heat seal.

In summary, this invention deals with a package for a medical instrument such as a needle assembly. The package includes a hollow shield having an open end for insertion and removal of at least a portion of a medical instrument and means to support and protect the instrument when it is contained therein. A cap is provided and is adapted to be mounted on the shield with an opening therein aligned with the opening in the shield to permit insertion and removal of the instrument with respect to the shield and cap. The cap is shiftable between a first position to cooperate with the shield in protecting the instrument and a second position exposing a portion of the instrument to facilitate grasping and removal thereof. Removable closure means covers the opening of the cap and shield and, when removed, exposes the opening in the cap and shield to permit insertion or removal of a medical instrument.

With the above objectives among others in mind reference is made to the attached drawings.

BRIEF DESCRIPTION OF THE DRAWINGS

In The Drawings:

FIG. 1 is a perspective view of the package of the invention with a needle assembly contained therein;

FIG. 2 is a sectional elevation view of the cap and closure portions of the package;

FIG. 3 is a partially sectional side elevation view of the package of the invention with a needle assembly contained therein and a portion of the package broken away and removed;

FIG. 4 is a partially sectional side elevation view thereof with the package in the closed and sealed condition;

FIG. 5 is a partially sectional side elevation view thereof with the package having been opened; and FIG. 6 is a perspective view of the cap and closure portions of the package of the invention with the closure having been substantially removed from the cap.

DETAILED DESCRIPTION

Package 20 is adaptable for use in protecting and maintaining in a sterile condition a number of different types of medical instruments. In the depicted embodiment it is designed for use in packaging a conventional type of disposable needle assembly including a cannula 22 mounted in a hub 24. The cannula 22 has a sharp pointed exposed end 26. The other end of the cannula is mounted in conventional fashion such as by epoxy in hub 24 with the open rear end 28 of the hub in communication with the opening in the needle thus providing a through passageway in the needle assembly. The hub is generally tubular in configuration and is designed to be coupled at its open end 28 with a conventional syringe or similar device.

Package 20 includes a tubular shield 30, a generally tubular cap 32 and a closure 34. Shield 30 has a closed end 36 and an open end 38. A flange 40 surrounds the open end of the shield. The shield 30 has a hollow interior and is dimensioned so that the needle 22 and a portion of the hub 24 of the needle assembly can be inserted therein until the outer tapered surface of the hub frictionally engages with the inner surface of the shield adjacent to open end 38. This frictional interengagement holds the needle assembly in fixed position with respect to the shield with the needle 22 and a portion of the hub 24 housed and protected within the shield. In fact, the needle 22 is spaced from the walls of the shield to provide additional protection to the needle and to alleviate the danger of the needle piercing the side walls of the shield. The upper end portion 42 of the hub extends rearwardly of open end 38 of shield 30 and is protected and surrounded by a portion of cap 32.

Cap 32 has a forward tubular portion 44 with an annular inner surface 46 closely approximating the outer dimension of shield 30 below flange 40. Three spaced sealing rings 48 are positioned on the inner surface 46 to engage with the outer surface of shield 30 when the shield is positioned in the cap. The number of sealing rings is a matter of choice. Sealing rings 48 can be molded in the inner surface 46 of cap 32 or, alternatively, they can be formed in other conventional ways such as by mounting gaskets of rubber, plastic or similar material in annular recesses in the cap. The shield is positioned within the cap by extending closed end 36 through the open upper end 50 of the cap and down through the open lower end 52 of the cap. The shield is extended until undersurface 54 of flange 40 engages with a radially extending annular shoulder 56 on the inner surface of cap 32. Lower portion 44 of the cap is positioned below shoulder 56 and is in sealing engagement with the outer surface of shield 36. In this condition, the cap is also slidable in an axial direction with respect to the shield.

The upper end portion 58 of cap 32 has a slightly wider outer diameter than lower portion 44 and has a rim 60 surrounding its upper end which forms upper open end 50 of the cap. The inner surface of portion 58 has a larger diameter than the inner surface of portion 44 and forms a cavity 62 to house flange 40 of the shield and the exposed portion 44 of hub 24. Cavity 62 is large enough to contain portion 42 and flange 40 when the undersurface 54 of flange 40 is seated on shoulder 56. Open end 50 is sealed by closure 34 which rests on the upper rim 64 of flange 60. It can be sealed in position by conventional means such as a heat sealing process. With closure 34 sealed in position closing opening 50, the needle assembly is in protected sealed position within package 20. The closure 34 forms a seal at one end and the sealing rings 48 in engagement with the outer surface of shield 30 form the seal at the other end.

All of the elements of package 20 can be formed of conventional, low cost, disposable materials. For example, shield 30 can be formed of polypropylene plastic, cap 32 of polyethylene plastic, and closure 34 of a well known surgical grade paper thus forming a heat sealable, peelable tab. Naturally other well known conventional substitutes for these materials are readily apparent and can be utilized in place of the mentioned materials for the package components. Use of the paper closure 34 permits ease of conventional sterilization procedures such as E.T.O. sterilization and the peelable tab also provides positive tamper evidence. A breaking of the heat seal is readily observable. Sterilization of the package is easily accomplished through closure 34 in the packaged condition as depicted in FIG. 4. The package is then in condition for shipping, handling, and storage without danger of destruction of the integrity and sterilized condition of the needle assembly housed therein.

The package can be opened for use without difficulty and without danger of damage to the needle assembly, injury to the user or contamination of the needle. As shown in FIG. 5, the user grasps package 20 and peels off closure 34. He then slides cap 32 relative to shield 30 in the permitted direction as shown by the arrow in FIG. 5 thereby exposing portion 42 of the hub 24 to the exterior of the package. He then can grasp the hub and remove the needle assembly from the package in ready to use condition. This rapid and simple procedure can be carried out by the user without difficulty while minimizing the danger of damage or contamination of the needle assembly and the surrounding area. The needle assembly and the package components are disposable after use.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A package for a medical instrument comprising; a hollow shield having an open end surrounded by a flange for insertion and removal of at least a portion of a medical instrument and means to support and protect the instrument when it is contained therein, a separate cap adapted to be mounted on the shield with an opening therein aligned with the opening in the shield to permit insertion and removal of the instrument with respect to the shield and cap, said cap being shiftable between a first position to cooperate with the shield in protecting the instrument and a second position exposing and positioning a portion of the instrument exteriorly of the package to facilitate grasping and removal thereof, wherein the cap is open at both ends, and has a shoulder on its inner surface intermediate the ends of the cap, the shield adapted to be extended through the opening in one end of the cap and to remain engaged with inner surfaces on the cap, the cap being in a first position and restricted from further movement in an upward direction by the underlying engagement of the lateral shoulder on the inner surface of the cap and the undersurface of the flange on the shield, the cap surrounding the portion of the hub extending from the shield when the cap is in the first portion, the cap being slidably shiftable to a second position with the shoulder on the cap being moved away from the flange on the shield and the cap in the second position exposing a portion of the hub extending from the shield to facilitate grasping of the hub and removal of the medical instrument from the shield, and removable closure means covering the opening in the cap and shield and, when removed, exposing the opening in the cap and shield to permit insertion of removal of a medical instrument.

2. The invention in accordance with claim 1 wherein the medical instrument is a needle assembly including a cannula having an open pointed end and an end mounted in the through passageway of a hub with the passageway in the cannula and the hub being in communication to provide a through passageway in the needle assembly.

3. The invention in accordance with claim 2 wherein the shield is tubular in configuration with a flange surrounding the open end thereof, the inner surface of the shield being tapered and dimensioned with respect to the hub of the needle assembly so that the needle assembly can be inserted through the open end of the shield until the needle and a portion of the hub is covered by the shield and a remainder of the hub extends outward of the open end of the shield, the hub being in frictional engagement with the inner wall surface of the shield.

4. The invention in accordance with claim 1 wherein at least one seal ring is positioned on the inner surface of the cap and is in engagement with the outer surface of the shield to provide a slidable seal between the cap and the shield.

5. The invention in accordance with claim 1 wherein the closure means includes a flexible closure mounted on the cap to cover the aligned openings in the cap and shield.

6. The invention in accordance with claim 5 wherein the closure is in the form of a paper tab, the shield being formed of polypropylene material and the cap being formed of polyethylene material.

* * * * *